United States Patent [19]

Terai et al.

[11] Patent Number: 5,036,836
[45] Date of Patent: Aug. 6, 1991

[54] LITHOTRIPTER WITH SHOCK-WAVE GENERATOR MOVEMENT MECHANISM

[75] Inventors: Fujio Terai; Atsushi Kinase, both of Yokohama, Japan

[73] Assignee: Kabushiki Kaisha Toshiba, Kawasaki, Japan

[21] Appl. No.: 450,397

[22] Filed: Dec. 14, 1989

[30] Foreign Application Priority Data

Dec. 15, 1988 [JP] Japan ................... 63-317097

[51] Int. Cl.⁵ .......................................... A61B 17/22
[52] U.S. Cl. .............................................. 128/24 EL
[58] Field of Search ............. 128/24 EL, 660.03, 804, 128/653 R, 660.003

[56] References Cited

U.S. PATENT DOCUMENTS

| | | | |
|---|---|---|---|
| 4,230,129 | 10/1980 | LeVeen | 128/804 |
| 4,763,652 | 8/1988 | Brisson et al. | 128/24 EL |
| 4,805,600 | 2/1989 | Wess et al. | 128/24 EL |

FOREIGN PATENT DOCUMENTS

| | | |
|---|---|---|
| 0185233 | 6/1986 | European Pat. Off. . |
| 0205878 | 12/1986 | European Pat. Off. . |
| 0269801 | 6/1988 | European Pat. Off. . |

OTHER PUBLICATIONS

EDAP Lithotripter Lt. 01 Technical Leaflet; Jun. 12, 1987, pp. 1-7.
Dornier Medical Systems (MPL 9000), Nov., 1987.

Primary Examiner—William E. Kamm
Assistant Examiner—Kevin Pontius
Attorney, Agent, or Firm—Oblon, Spivak, McClelland, Maier & Neustadt

[57] ABSTRACT

A control processing device moves an X-/Y-/Z-axis movement mechanism, a first rotation mechanism, and a second rotation mechanism. Consequently, a shock-wave oscillating device is moved in X-, Y- and Z-directions, so that the direction of radiation of shock waves can be changed while the focal point of the shock waves is being set at a target of treatment.

8 Claims, 6 Drawing Sheets

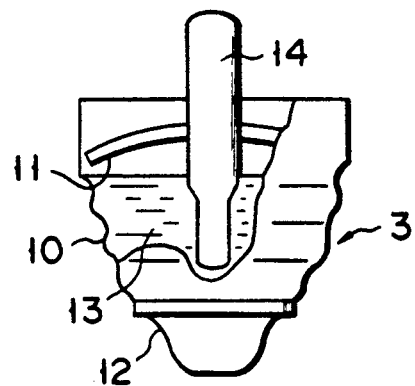
F I G. 2
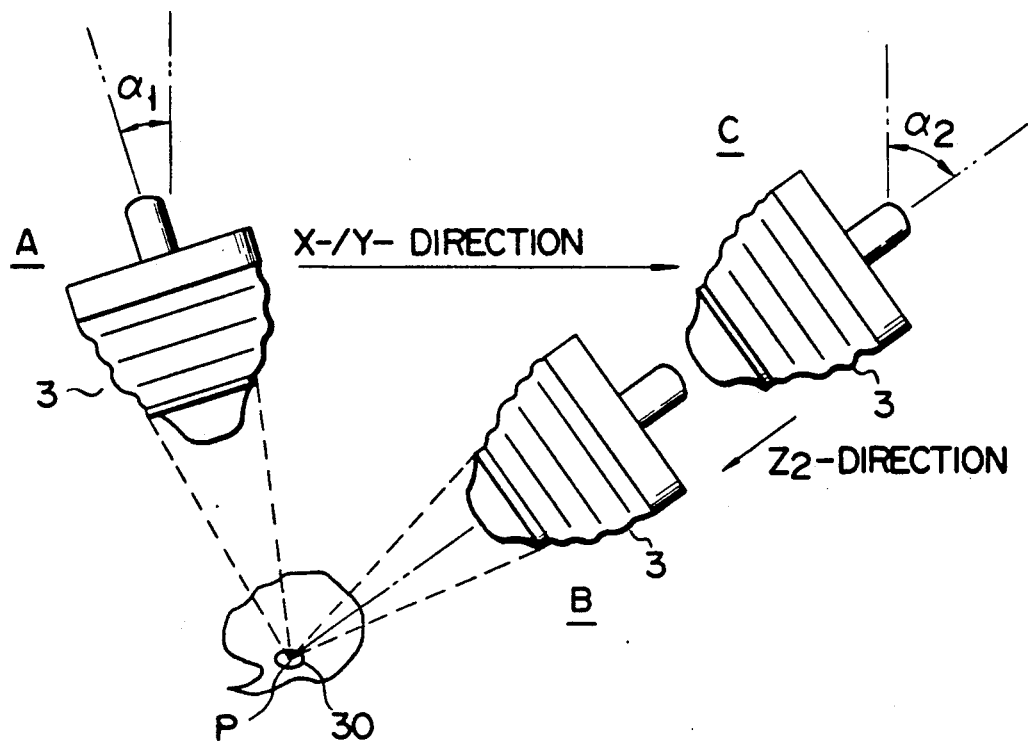
F I G. 3

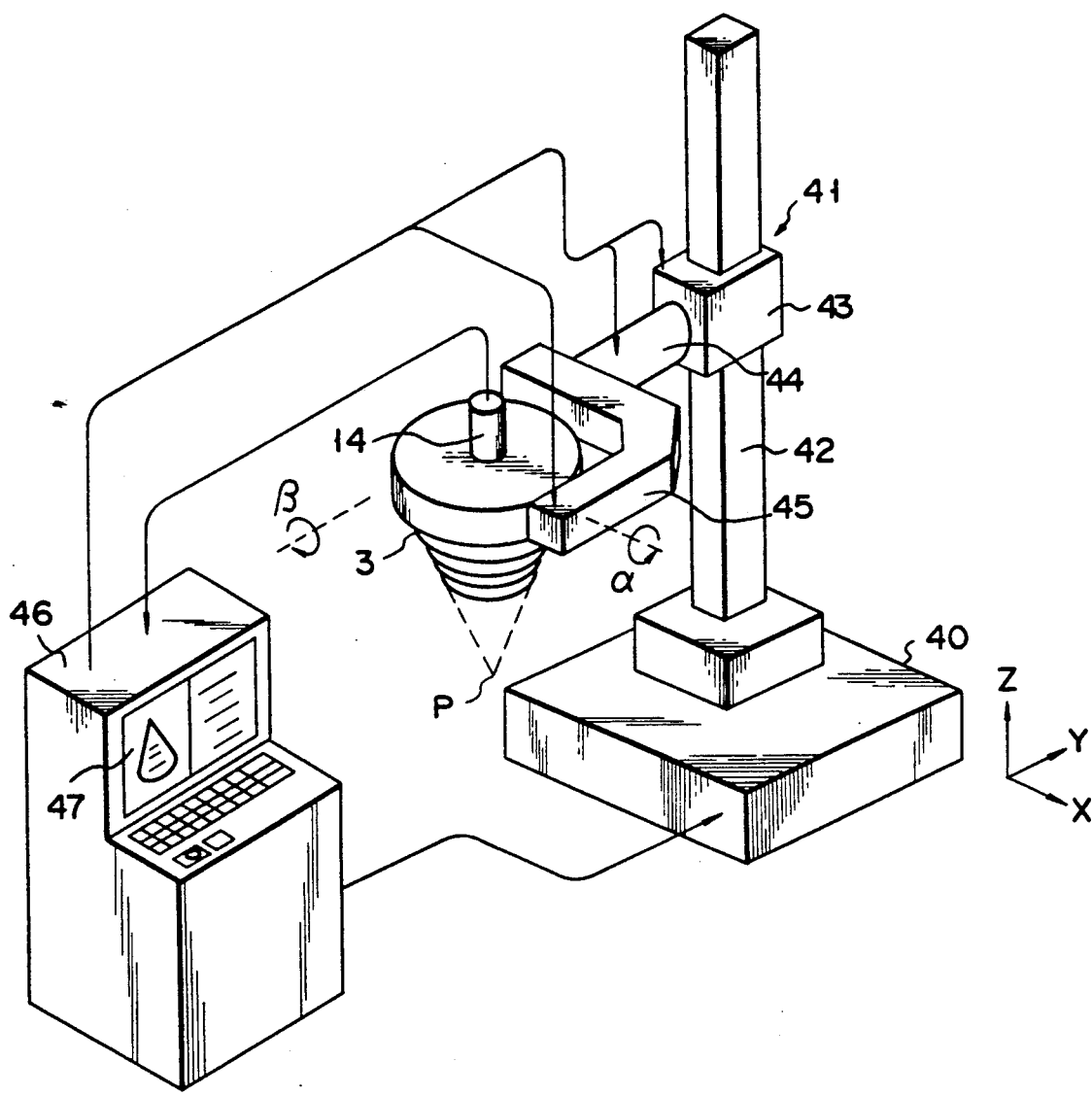
F I G. 7

LITHOTRIPTER WITH SHOCK-WAVE GENERATOR MOVEMENT MECHANISM

BACKGROUND OF THE INVENTION

1. Field of the Invention

The present invention relates to a shock-wave medical treatment apparatus for destroying, for example, a kidney stone or a gallstone in a subject, by using shock waves.

2. Description of the Related Art

In a shock-wave medical treatment apparatus, shock waves emitted from a shock-wave oscillator section is focused on a target of treatment in a subject, for example, a kidney stone or a gallstone. The shock waves are sent to destroy the kidney stone, or the like.

The direction of radiation of shock waves is sometimes changed by moving the shock-wave oscillator section, after the focal point of shock waves has been set. A target of treatment differs from subject to subject. Thus, if the direction of radiation of shock waves is changed, the focal point of shock waves is displaced from the target.

SUMMARY OF THE INVENTION

An object of the present invention is to provide a shock-wave medical treatment apparatus, wherein after the focal point of shock waves has been initially set, the direction of radiation of shock waves can be easily changed, while the focal point is being fixed at a target of treatment which differs from subject to subject.

The present invention provides a shock-wave medical treatment apparatus comprising: shock-wave oscillating section for emitting shock waves; X-/Y-/Z-axis movement means for moving the shock-wave oscillating means in X-, Y- and Z-directions; first rotation means, attached to an end portion of the X-/Y-/Z-axis movement means, for rotating the shock-wave oscillating means in a first direction with respect to a target of treatment in a subject; second rotation means, attached to the first rotation means, for rotating the shock-wave oscillating means in a second direction crossing the first direction; and control processing means for driving the X-/Y-/Z-movement means, the first rotation means and the second rotation means to change the direction of radiation of the shock waves, while the shock-wave oscillating means is being directed to the target of treatment.

According to the invention, the control processing device moves the X-/Y-/Z-axis movement mechanism, the first rotation mechanism, and the second rotation mechanism. Consequently, the shock-wave oscillating device is moved in X-, Y- and Z-directions, so that the direction of radiation of shock waves can be changed while the focal point of the shock waves is being set at a target of treatment.

BRIEF DESCRIPTION OF THE DRAWINGS

FIG. 2 shows a structure of a shock-wave oscillator section;

FIG. 3 shows the shock-wave oscillator section in the case where the direction of radiation of shock waves is changed;

FIG. 7 shows a structure of the shock-wave medical treatment apparatus wherein an X-/Y-/Z-axis movement mechanism is modified;

DETAILED DESCRIPTION OF THE PREFERRED EMBODIMENTS

Figure 1:
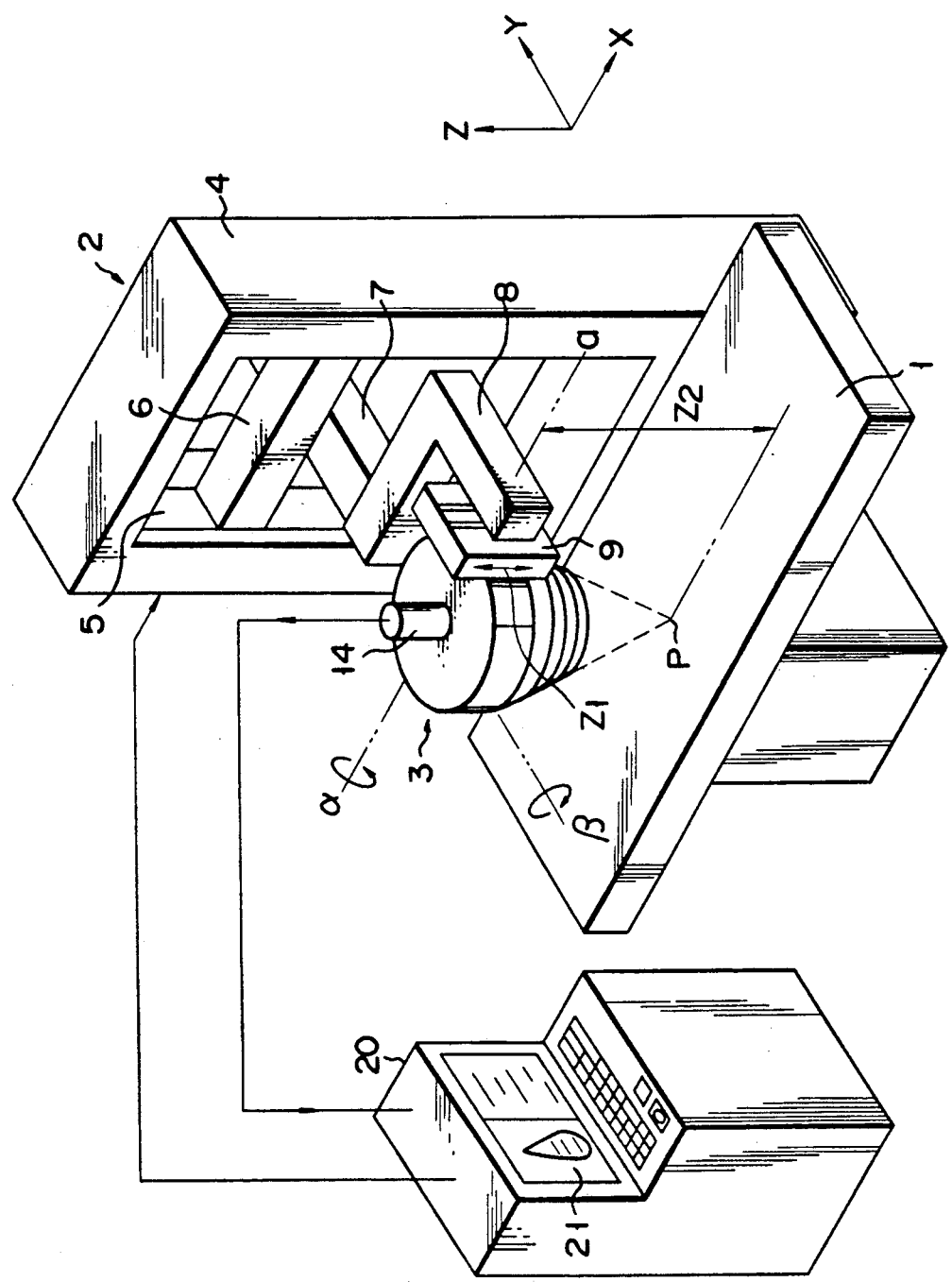
FIG. 1 shows a structure of a shock-wave medical treatment apparatus according to an embodiment of the present invention.

FIG. 1 shows a structure of a shock-wave medical treatment apparatus according to an embodiment of the present invention. In FIG. 1, an X-/Y-/Z-axis movement mechanism 2 is arranged adjacent to a bed 1. The X-/Y-/Z-axis movement mechanism 2 serves to move a shock-wave oscillator section 3 for radiating shock waves in the X-, Y-, an Z-directions. The movement mechanism 2 has a frame 4. The frame 4 has, in its mutually facing inner faces, guide grooves 5 extending in the Z-direction. A first arm 6 is slidably set in the guide grooves 5. A second arm 7 is slidably attached to the first arm 6 in the X- and Y-directions. An L-shaped arm 8, serving as a first rotation mechanism, is attached to one end of the second arm 7. The L-shaped arm 8 is rotatable in the $\beta$-direction, in relation to the second arm 7. The $\beta$-direction describes a circle in a plane perpendicular to the Y-direction. The other end of the L-shaped arm 8 is provided with a movement adjustment mechanism 9 via a second rotation mechanism. The mechanism 9 is connected to the shockwave oscillator section 3. The mechanism 9 is rotatable in the $\alpha$-direction in relation to the L-shaped arm 8. The $\alpha$-direction describes a circle in a plane perpendicular to the X-direction.

FIG. 2 shows a structure of the shock-wave oscillator section 3. A bellows 10 is connected, at one end, to a shock-wave oscillator 11, and, at the other end, to a rubber water bag 12. A closed chamber defined by the bellows 10, shock-wave oscillator 11 and water bag 12 is filled with water 13. Also, the a probe 14 of an ultrasonic diagnostic apparatus is inserted into the closed chamber.

A control processor 20 supplies movement control signals to the X-/Y-/Z-axis movement mechanism 2, the L-shaped arm 8 and the mechanism 9, respectively. The control processor 20 receives a detection signal from the probe 14 and causes a display 21 to display a corresponding image. Each movement control signal is obtained on the basis of the amount of movement in the X-, Y-, and Z-axis directions. A mechanism comprising the X-/Y-/Z-axis movement mechanism 2, the L-shaped arm 8 and the mechanism 9 has six degrees of freedom, four of these being X, Y, Z1, Z2 (linear movement), and the other two being $\alpha$ and $\beta$ (rotational movement). The degree of freedom Z1 corresponds to the Z-axis of the X-/Y-/Z-axis movement mechanism 2, and the degree of freedom Z2 corresponds to the movement axis of the mechanism 9. The focal point (destruction point) P of shock waves radiated from the shockwave oscillator section 3 can be found by solving the coordinate transformation matrix of the degrees of freedom of linea movement, X, Y, Z1 and Z2, and the degrees of freedom of rotational movement, $\alpha$ and $\beta$. Namely, the focal point P is given by the following equation:

$$\begin{bmatrix} Px \\ Py \\ Pz \end{bmatrix} = \begin{bmatrix} X \\ Y \\ Z1 \end{bmatrix} + \begin{bmatrix} \cos\beta & 0 & \sin\beta \\ 0 & 1 & 0 \\ -\sin\beta & 0 & \cos\beta \end{bmatrix} \begin{bmatrix} 1 & 0 & 0 \\ 0 & \cos\alpha & -\sin\alpha \\ 0 & \sin\alpha & \cos\alpha \end{bmatrix} \begin{bmatrix} 0 \\ 0 \\ -Z2 \end{bmatrix}$$

$$= \begin{bmatrix} X - Z2 \cdot \sin\beta \cdot \cos\alpha \\ Y + Z2 \cdot \sin\alpha \\ Z1 - Z2 \cdot \cos\beta \cdot \cos\alpha \end{bmatrix} \quad (1)$$

The focal point P, obtained by the above equation, is represented by (Px1, Py1, Pz1). When the direction of radiation of shock waves is changed in this state, the focal point P is represented by (Px2, Py2, Pz2). When it is considered that the direction of radiation of shock waves is changed without changing the focal point, the following relationship is established:

$$\begin{bmatrix} P_{x1} \\ P_{y1} \\ P_{z1} \end{bmatrix} = \begin{bmatrix} P_{x2} \\ P_{y2} \\ P_{z2} \end{bmatrix}$$

From this relationship and equation (1), the following equations are obtained:

$$X_1 - Z2_1 \cdot \sin\beta_1 \cdot \cos\alpha_1 = X_2 - Z2_2 \cdot \sin\beta_2 \cdot \cos\alpha_2 \quad (2)$$

$$Y_1 + Z2_1 \cdot \sin\alpha_1 = Y_2 + Z2_2 \cdot \sin\alpha_2 \quad (3)$$

$$Z1_1 - Z2_1 \cdot \cos\beta_1 \cdot \cos\alpha_1 = Z1_2 - Z2_2 \cdot \cos\beta_2 \cdot \cos\alpha_2 \quad (4)$$

In the above equations, X1 and Y1 indicate the position of the shock-wave oscillator section 3 before movement, $\alpha 1$ and $\beta 1$ denote angles of the shock-wave oscillator section 3, and $Z2_1$ denotes the position of the mechanism 9. Also, X2 and Y2 represent the position of the shock-wave oscillator section 3 after the movement, $\alpha 2$ and $\beta 2$ indicate the angles of the shockwave oscillator section 3 at this time, and $Z2_2$ indicates the position of the mechanism 9 after the movement.

The shock-wave oscillator section 3 is moved in the Z-direction while the water bag 12 is being in contact with the subject. In this case, the the shock-wave oscillator section 3 is moved in the Z-direction by the operation of the mechanism 9, and at this time the first arm 6 is fixed in the Z-direction. The movement of the first arm 6 in the Z-direction is fixed, since the degree of freedom in the Z-direction is unnecessarily great because of Z1 and Z2. In the equation (4), the relationship between $Z1_1$ and $Z1_2$ is represented by:

$$Z1_1 = Z1_2$$

Thus, the equation (4) is developed as follows:

$$T2_2 = Z2_1 \cdot \cos\alpha_1 \cdot \cos\beta_1 + (\cos\alpha_2 \cdot \cos\beta_2) \quad (5)$$

As can be seen from the equation (5), in order to exactly adjust the focal point P, it is necessary to vary the value Z2. If equation (2) is substituted in equation (5), the amount of movement $\Delta X$ is given by:

$$\Delta X = Z2_1 \cdot \cos\alpha_1 \cdot \sin\Delta\beta + \cos\beta_2 \quad (6)$$

where
$\Delta X = X2 - X1$
$\Delta\beta = \beta 2 - \beta 1$

Similarly, if equation (5) is substituted in equation (3), the amount of movement $\Delta Y$ is given by:

$$\Delta Y = -Z2_1 \cdot -\sin\alpha_1 - Z2_1(\cos\alpha 1 \cos\beta 1/\cos\alpha 2 \cos\beta 2) \times \sin\alpha_2 \quad (7)$$

where $\Delta Y = Y2 - Y1$

From equation (5), Z2 is given by:

$$\Delta Z2 - Z2_1((\cos\alpha 1 \cos\beta 1/\cos\alpha 2 \cos\beta 2) - Z2_1 \quad (8)$$

where $\Delta Z2 = Z2_2 - Z2_1$

The control processor 20 calculates the amount of movements $\Delta X$, $\Delta Y$ and $\Delta Z2$, from equations (6) and (8), and, based on the calculated values, supplies movement control signals to the X-/Y-/Z-axis movement mechanism 2 and the mechanism 9.

The operation of the apparatus having the above structure will now be described.

First, a patient or a subject lies on the bed 1. Then, the control processor 20 sends movement control signals to the X-/Y-/Z-axis movement mechanism 2. Upon actuation of the movement mechanism 2, the shock-wave oscillator section 3 is lowered. Once the water bag 12 of the shock-wave oscillator section 3 is brought into contact with the subject, the control processor 20 stops the lowering of the X-/Y-/Z-axis movement mechanism 2 and starts to operate the probe 14. The probe 14 scans the interior of the subject, and outputs a detection signal. The detection signal is sent to the control processor 20. The control processor 20 converts the detection signal to an image and enables the display 21 to display the image. The control processor 20 supplies the movement control signals to the X-/Y-/Z-axis movement mechanism 2 constantly, thereby keeping the display 21 displaying the interior of the subject. The shockwave oscillator section 3 is moved in the X-, Y-, and Z-directions by the operation of the X-/Y-/Z-axis movement mechanism. While the shock-wave oscillator sectio 3 is being moved, the image obtained through the probe 14 is displayed on the display 21. When a target 30 of treatment—for example, a kidney stone—is displayed on the display 21 in this manner, the focal point P of the shock-wave oscillator section 3 is set to the position of the kidney stone. In this case, the position of the shock-wave oscillator section 3 is adjusted in the $\alpha$- and $\beta$-directions in order for shock-waves not to adversely affect other bodily parts, such as ribs.

A description will now be given of the case where the shock-wave oscillator section 3 is moved from position A to position B. In position A, shock waves are radiated at an angle $\alpha 1$, and in position B, shock waves are radiated at an angle $\alpha 2$. The control processor 20 supplies the X-/Y-/Z-axis movement mechanism 2 with movement control signals corresponding to the amounts of movement $\Delta X$, $\Delta Y$ and $\Delta Z2$. The movement mechanism 2 moves the shock-wave oscillator section 3 in the X-/Ydirection and rotates the shock-wave oscillator section 3 in the $\alpha$-direction. Simultaneously, the mechanism 9 moves in the Z2-direction, thereby setting the focal point P of the shock-wave oscillator section 3 at the target 30. The positioning between the focal point P of the shock-wave oscillator section 3 and the target 30 may be carried out in the following manner. First, the shock-wave oscillator section 3 is moved in the X-/Y-direction, and is rotated in the c-direction by the L-shaped arm 8. Then, the mechanism 9 is moved in the Z2-direction to set the focal point P of the shock-wave oscillator section 3 at the target 30. At this time, despite the movement of the shock-wave oscillator 3, the the target 30 is made to remain in the visual field of the probe 14. The probe 14, during movement, detects the target 30. Thus, in the ultrasonic diagnostic apparatus, the target 30 is not lost. When the local point P of the shock-wave oscillator section 3 is set at the target 30 in position B, the shock-wave oscillator section 3 sends shock waves through the kidney stone in such a direction that no influence is exerted on the ribs.

As has been described above, in the first embodiment, the shock-wave oscillator section 3 is moved in the X-, Y- and Z-directions by the X-/Y-/Z-axis movement mechanism 2. Then, the shock-wave oscillator section 3 is rotated in the $\alpha$ and $\beta$-directions by the L-shaped arm 8 and the mechanism 9. With the operation of the mechanism 9, the distance Z2 between the subject and the shock-wave oscillator section 3 is adjusted. Thus, even if the direction of radiation of shock waves is changed in accordance with the movement of the shock-wave oscillator section 3, the focal point P of shock waves is made to remain on the target 30. Though a slender patient and a stout patient have different positions of target 30, the focal point P of the shock-wave oscillator section 32 can be easily and exactly set at the target 30 in various directions. In addition, the structure of the mechanism for moving the shock-wave oscillator section 3, which is constituted by the X-/Y-/Z-axis movement mechanism 2, L-shaped arm 8 and mechanism 9, is very simple.

The shock-wave oscillator section 3 may be moved by means of a single joystick (two-axis type). In this case, the amounts of movement $\Delta\alpha$ and $\Delta\beta$ are input to the control processor 20 by means of the joystick. The control processor 20 executes arithmetic operations of equations (6) to (8), on the basis of the amounts of movement $\Delta\alpha$ and $\Delta\beta$, and finds the amounts of movement $\Delta X$, $\Delta Y$ and $\Delta Z2$. In this way, with the use of the joystick, the shock-wave oscillator section 3 can change its direction of radiation of shock waves, while keeping the focal point at the target.

A second embodiment of the present invention will now be described.

Figure 4:
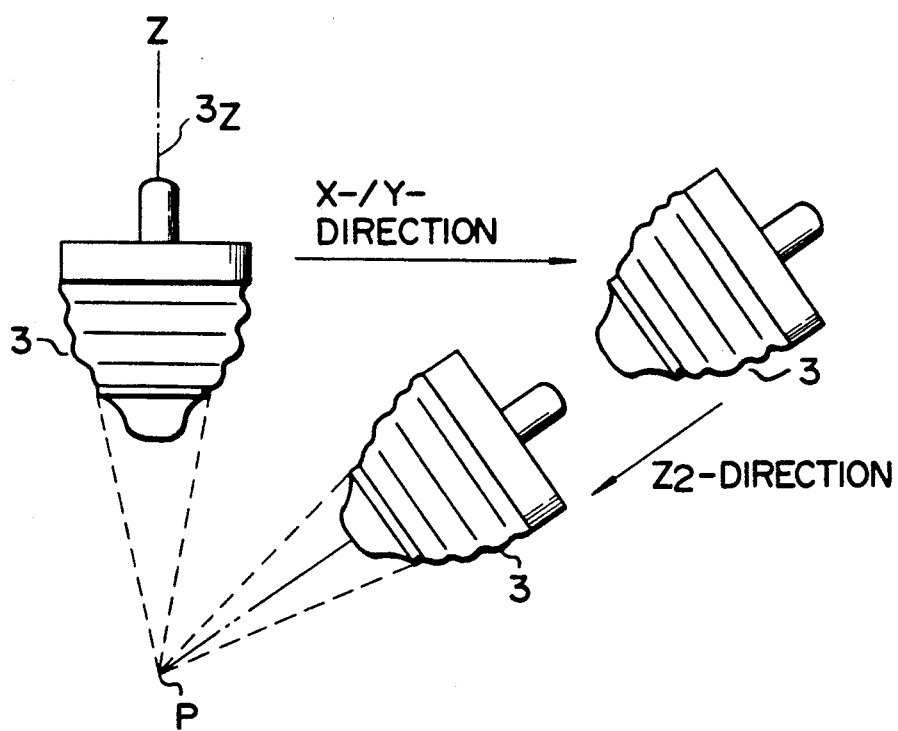
FIG. 4 shows the shock-wave oscillator section in the case where the position of the shock-wave oscillator section set in parallel to the Z-axis is changed so that the direction of radiation of shock waves is changed.

FIG. 4 shows the initial state of the shock-wave oscillator section 3 whose main axis 3z is set in parallel to the Z-direction. When the direction radiation is changed, the control processor 20 calculates the following amounts of movement, from equation (1):

$$\begin{bmatrix} Px \\ Py \\ Pz \end{bmatrix} = \begin{bmatrix} -Z2\cos\alpha\sin\beta + x \\ Z2\sin\alpha + y \\ -Z2\cos\alpha\cos\beta + Z1 \end{bmatrix} \quad (9)$$

When the $\alpha$- and $\beta$-directions are changed without changing the focal point P, the amounts of movement X, Y and Z2 are found by substituting the following in equation (9):

$(Px, Py, Pz)^t = (0, 0, -Z2)^T$

Namely, equation (9) is developed as follows:

$X = Z2 \cdot \sin\beta \cdot \cos\alpha$ $Y = -Z2 \cdot \sin\alpha$ $Z2 = Z1/(\cos\alpha \cdot \cos\beta - 1) \quad (10)$ Thus, when the shock-wave oscillator section 3 is rotated by given angles in the $\alpha$ and $\beta$ directions, without changing the focal point P, the control processor 20 outputs the movement control signals to the X-/Y-/Z-axis movement mechanism in accordance with the amounts of movement X, Y and Z2.

By virtue of the structure of control processor 20, the shock-wave oscillator section 3 can be easily moved, in particular, when the direction of radiation of shock waves is changed from the state wherein the shock-wave oscillator section 3 is set in parallel to the X-direction. In addition, in this second embodiment, like in the first embodiment, the amounts of movement $\Delta\alpha$ and $\Delta\beta$ may be input to the control processor 20 by means of a joystick, thereby changing the direction of shock waves radiated from the shock-wave oscillator section 3.

A third embodiment of the present invention will now be described. The apparatus according to the third embodiment has a simpler control function. In this case, the shock-wave oscillator section 3 moves very slightly.

When the shock-wave oscillator section 3 is moved slightly from a given position ($\alpha 1$, $\oplus 1$, $Z2_1$) by a degree represented by:

$\cos\Delta\alpha = 1$, $\cos\Delta\beta = 1$, $\sin\Delta\alpha = \Delta\alpha$, $\sin\Delta\beta = \Delta\beta$, the following equations can be obtained by approximation equations (6) to (8):

$\Delta X = Z2_1(\cos\alpha 1/\cos\beta 1) \cdot \Delta\beta \quad (11)$ $\Delta Y = -Z1_1(1/\cos\alpha 1) \; \Delta\alpha \quad (12)$ $\Delta Z2 = Z2_1(\Delta\alpha \cdot \tan\alpha 1 + \Delta\beta \cdot \tan\beta 1) \quad (13)$ These equations indicate that, if values determined by a given position are considered to be proportion constants, the values $\Delta X$, $\Delta Y$, $\Delta Z2$, $\Delta\alpha$, and $\Delta\beta$ have a linear relationship. Supposing these proportion constants are A, B, C and D, equations (11) to (13) are developed as follows:

$\Delta X = A \cdot \Delta\beta \quad (14)$ $\Delta Y \Delta B \cdot \Delta\alpha \quad (15)$ $\Delta Z2 = C \; \Delta\beta + D \cdot \Delta\alpha \quad (16)$ From equations (14) to (16), the amounts of movement $\Delta X$, $\Delta Y$ and $\Delta Z2$ can be found by simple proportional calculations. The movement control signals corresponding to $\Delta X$, $\Delta Y$ and $\Delta Z2$ are sent to the X-/Y-/Z-axis movement mechanism 2 and mechanism 9.

As described above, in the third embodiment, the control processor 20 has a control function using simple proportional calculations based on a trigonometric function. Thus, when the shock-wave oscillator section 3 is moved slightly, the amounts of movement $\Delta X$, $\Delta Y$ and $\Delta Z2$ are calculated by a simple process, and the corresponding movement control signals can be output. Namely, the structure of the control processor 20 is simplified.

If the amounts of movement in a unit time are considered, the speeds X, Y, Z2, $\alpha$ and $\beta$ corresponding to the amounts of movement are given by:

$$X = A \cdot B \tag{17}$$

$$Y = B \cdot A \tag{18}$$

$$Z2 = C \cdot \beta + D \cdot \alpha \tag{19}$$

Thus, the operation of the control processor 20 can be related to the speed control.

In addition, in this third embodiment, like in the first embodiment, the amounts of movement $\Delta\alpha$ and $\Delta\beta$ may be input to the control processor 20 by means of a joystick, thereby changing the direction of shock waves radiated from the shock-wave oscillator section 3.

A fourth embodiment of the present invention will now be described.

In the fourth embodiment, the shock-wave oscillator section 3 is moved from the position where the oscillator section 3 is set in parallel to the Z-direction. In this case, the shock-wave oscillator section 3 is hardly rotated in the $\alpha$- or $\beta$-direction, and is slightly moved in the X-, Y- and Z-directions.

In this case, $$\alpha, \beta \approx 0$$

$$\therefore \cos\alpha \approx 1$$

$$\sin\beta \approx \beta$$

If this relationship is substituted in equation (9), the following equation is obtained:

$$\begin{bmatrix} Px \\ Py \\ Pz \end{bmatrix} = \begin{bmatrix} -Z2 \cdot \beta + x \\ Z2 \cdot \alpha + y \\ -Z2 + Z1 \end{bmatrix} \tag{20}$$

In order to emit shock waves at given angles $\alpha$ and $\beta$, without changing the focal point P of the shock-wave oscillating section 3, the following is given:

$$(Px, Py, Pz)^T = (0, 0, -Z2)^T$$

From this, the amounts of movements x', y' and z' in the respective directions are given by equation 21:

$$x' = Z2 \cdot \beta$$

$$y' = -Z2 \cdot \alpha$$

$$z' = 0$$

Thus, the control processor 20 outputs movement control signals for moving the shock-wave oscillator section 3 in the X- and Y-directions by the amounts of movement x', y' and z', thereby radiating shock waves to the target at angles $\alpha$ and $\beta$. Therefore, even when the shock-wave oscillator section 3 is hardly rotated in the $\alpha$ or $\beta$-direction, the same effects as the above embodiments can be obtained.

A fifth embodiment of the present invention will now be described.

In the fifth embodiment, the amounts of movement $\Delta X$, $\Delta Y$ and $\Delta Z$ calculated by the control processor 20 are expressed by adding constants F, G, H and I to equations (14) to (16):

$$\Delta X = (A + F) \cdot \Delta\beta \tag{22}$$

$$\Delta Y = (B + G) \cdot \Delta\alpha \tag{23}$$

$$\Delta Z2 = (C + H) \cdot \Delta\beta + (D + I) \cdot \Delta\alpha \tag{24}$$

Figure 5:
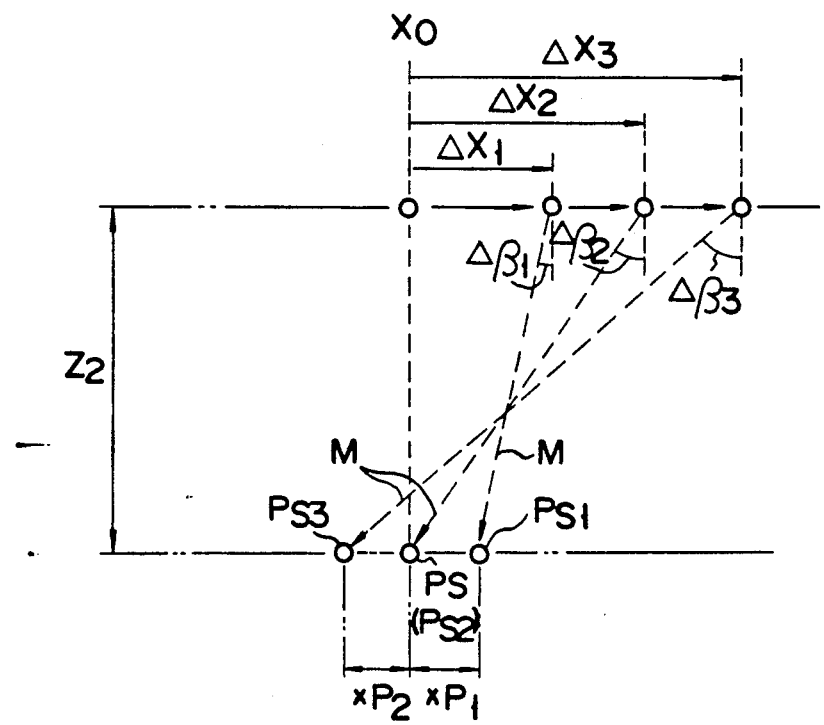
FIG. 5 illustrates positional errors of the shockwave oscillator section when it is moved.

For example, as shown in FIG. 5, the shock-wave oscillator section 3 is initially set in position X0. At this time, the focal point Ps coincides with the target. From this state, in order to change the direction of radiation of shock waves, the shock-wave oscillator section 3 rotates about the $\beta$-axis by an angle $\Delta\beta1$. At this time, the shock-wave oscillator section 3 receives from the control processor 20 a movement control signal representative of the amount of movement:

$$\Delta X1 = (A + F) \cdot \Delta\beta1$$

Thus, the shock-wave oscillator section 3 moves in the X-direction by $\Delta X1$. Simultaneously, the shock-wave oscillator section 3 is moved by the mechanism 9 in an M-direction by the amount of degree represented $$\Delta Z2_1 = (C + H) \cdot \Delta\beta1 + (D + I) \cdot \Delta\alpha1$$

At this time, the focal point is Ps1, and there occurs an error of Xp1 in the X-direction. In other words, while the shock-wave oscillator section 3 rotates in the $\beta$-direction by $\Delta\beta2$, the error in the X-direction increases from 0 to xp1.

When the shock-wave oscillator section 3 rotates by $\Delta\beta2$, the control processor 20 outputs to the X-/Y-/Z-axis movement mechanism 2 the movement control signal representative of the amount of movement given by:

$$\Delta X2 = (A + F) \cdot \Delta\beta2$$

Thus, the shock-wave oscillator section 3 is moved by the movement mechanism 2 by $\Delta X2$. Simultaneously, the shock-wave oscillator section 3 is moved by the mechanism 9 in an M-direction by the amount of degree represented by:

$$\Delta Z2_2 = (C + H) \quad \Delta\beta2 + (D + I) \cdot \Delta\alpha2$$

At this time, the focal point is Ps2, and there occurs no error in the X-direction. In other words, while the shock-wave oscillator section 3 rotates in the $\beta$-direction from $\Delta\beta1$ to $\Delta\beta2$, the error in the X-direction decreases from xp1 to 0.

Further, when the shock-wave oscillator section 3 rotates by $\Delta\beta3$, the control processor 20 outputs to the X-/Y-/Z-axis movement mechanism 2 the movement control signal representative of the amount of movement given by:

$$\Delta X3 = (A + F) \cdot \Delta\beta3$$

Thus, the shock-wave oscillator section 3 is moved by the movement mechanism 2 by $\Delta X3$. Simultaneously, the shock-wave oscillator section 3 is moved by the mechanism 9 in the $\Delta Z2$-direction, i.e., in an M-direction of the movement mechanism 38 by the amount of degree represented by:

$$\Delta Z2_3 = (C + H) \cdot \Delta\beta3 + (D + I) \cdot \Delta\alpha3$$

At this time, the focal point is Ps3, and the error in the X-direction increases from 0 to xp2. However, the direction of the error is opposite, compared to the case of $\Delta X1$.

Figure 6:
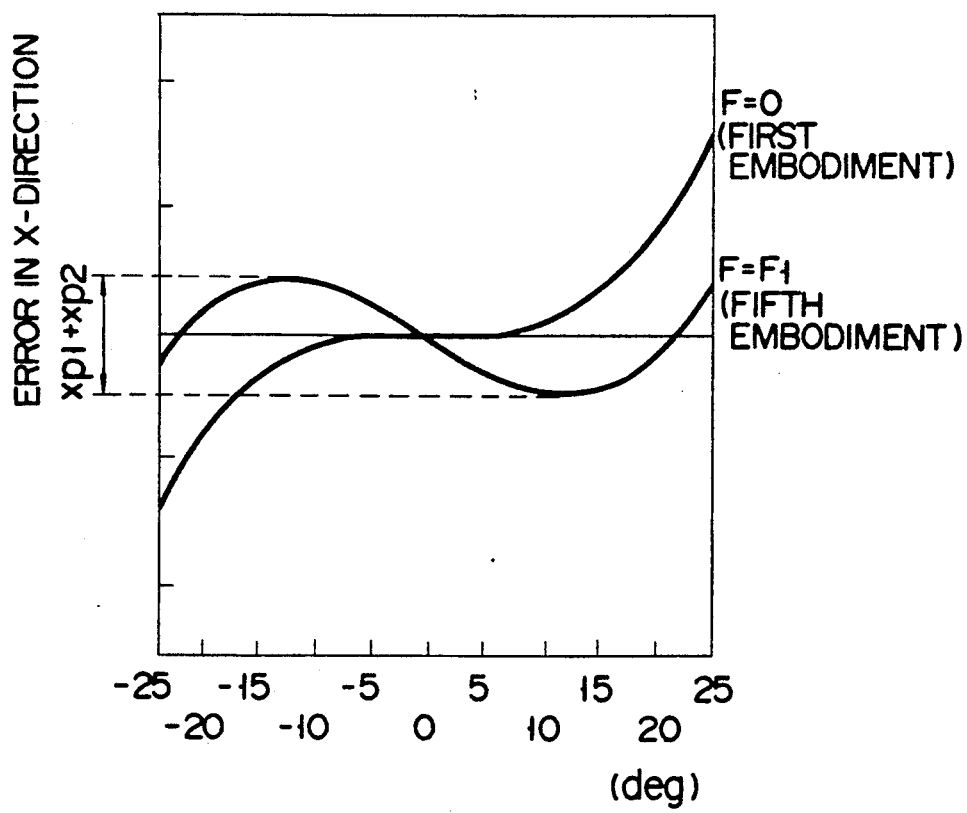
FIG. 6 shows comparative data relating to positional errors of the shock-wave oscillator section when it is moved.

As stated above, the error due to the trigonometric approximation occurs in both positive and negative directions with respect to the target of medical treatment. If the value F is suitably set, the absolute value of the error is made constant. Namely, with respect to the rotation of $\pm\Delta\beta3$ can be limited to $\pm xp1$. FIG. 6 shows the errors in the X-direction in the case where the shock-wave oscillator section is rotated by $\pm 25°$ in the $\beta$-direction in the first embodiment and the fifth embodiment. As shown in FIG. 6, when the rotation is slight (about 0°), the first embodiment is more effective. However, when the rotation is great, the fifth embodiment is more effective and the error can be reduced over a wider range of angle.

A sixth embodiment of the present invention will now be described.

In FIG. 7, a Z-axis movement mechanism 41 is mounted on an X-/Y-axis movement mechanism 40. The Z-axis movement mechanism 41 comprises a Z-axis column 42 set on the X-/Y-axis movement mechanism 40, and a moving body 43 slidably fitted on the Z-axis column 42. A first rotation means or a first arm 44, which is rotatable in the $\beta$-direction, is coupled at one end to the moving body 43. The first arm 44 is coupled, at the other end, to an L-shaped arm 45. A shock-wave oscillator section 3 is attached to the L-shaped arm 45 via a second rotation mechanism. Though the second rotation mechanism is not shown in FIG. 7, it is rotatable in the $\alpha$-direction perpendicular to the $\beta$-direction.

A control processor 46 supplies movement control signals to the X-/Y-axis movement mechanism 40, moving body 43, first arm 44 and second rotation mechanism, thereby changing the direction of radiation of shock waves while the focal point P of shock waves emitted from shock-wave oscillator section 3 is made to remain at the target. The control processor 46 receives a detection signal from a probe 14 and converts it to an image signal. An image corresponding to the image signal is displayed on a display 47.

The amounts of movement in the X-, Y- and Z-directions, in the case where the direction of radiation of shock waves is changed without changing the focal point P of shock-wave oscillator section 3, can be found in the following manner. The mechanism for moving the shock-wave oscillator section 3 has five degrees of freedom in the X-, Y- and Z-axes (linear movement) and the $\alpha$- and $\beta$-axes (rotational movement). The focal point P of shock-wave oscillator section 3 can be found by solving a coordinate transformation matrix of the degrees of freedom X, Y, Z, $\alpha$ and $\beta$. The focal point P is represented by XYZ-coordinates (Px, Py, Pz) as follows:

$$\begin{bmatrix} Px \\ Py \\ Pz \end{bmatrix} = \begin{bmatrix} \cos\beta & 0 & \sin\beta \\ 0 & 1 & 0 \\ -\sin\beta & 0 & \cos\beta \end{bmatrix} \begin{bmatrix} 1 & 0 & 0 \\ 0 & \cos\alpha & -\sin\alpha \\ 0 & \sin\alpha & \cos\alpha \end{bmatrix} \begin{bmatrix} 0 \\ 0 \\ -Zf \end{bmatrix} + \begin{bmatrix} x \\ y \\ z \end{bmatrix} \quad (25)$$

In equation 25, Zf denotes a distance between the rotation center of the $\alpha$-axis and the focal point P.

The focal point P set at the target before the shock-wave oscillator section 3 is moved is represented by (Px1, Py1, Pz1), and at this time the rotation angles are $\alpha 1$ and $\beta 2$. The focal point P after the shock-wave oscillator section 3 is moved is represented by (Px2, Py2, Pz2), and at this time the rotation angles are $\alpha 2$ and $\beta 2$. Since the focal point does not vary even if the direction of radiation of shock waves is changed, the following relationship is established:

$$\begin{bmatrix} P_{x1} \\ P_{y1} \\ P_{z1} \end{bmatrix} = \begin{bmatrix} P_{x2} \\ P_{y2} \\ P_{z2} \end{bmatrix}$$

and, $\alpha_1 \neq \alpha_2$ $\beta_1 \neq \beta_2$

From this relationship and equation (1), the amounts of movement $\Delta X$, $\Delta Y$, and $\Delta Z$ can be found:

$$\Delta X = Zf(\sin\beta 2 \cos\alpha 2 - \sin\beta 1 \cos\alpha 1) \quad (26)$$

$$\Delta Y = -Zf(\sin\alpha 2 - \sin\alpha 1) \quad (27)$$

$$\Delta Z = Zf(\cos\beta 2 \cos\alpha 2 - \cos\beta 1 \cos\alpha 1) \quad (28)$$

Accordingly, $$\Delta X = P_{x2} - P_{x1}$$

$$\Delta Y = P_{y2} - P_{y1}$$

$$\Delta Z = P_{z2} - P_{z1}$$

Thus, the control processor 46 calculates the amounts of movement $\Delta X$, $\Delta Y$ and $\Delta Z$, on the basis of equations (26) to (28). In accordance with these calculated amounts, the control processor 46 supplies movement control signals to the X-/Y-axis movement mechanism 40, moving body 43, first arm 44 and second rotation mechanism. A bed for medical treatment is arranged under the shock-wave oscillator section 3.

The operation of the apparatus having the abovedescribed structure will now be described.

Figure 8:
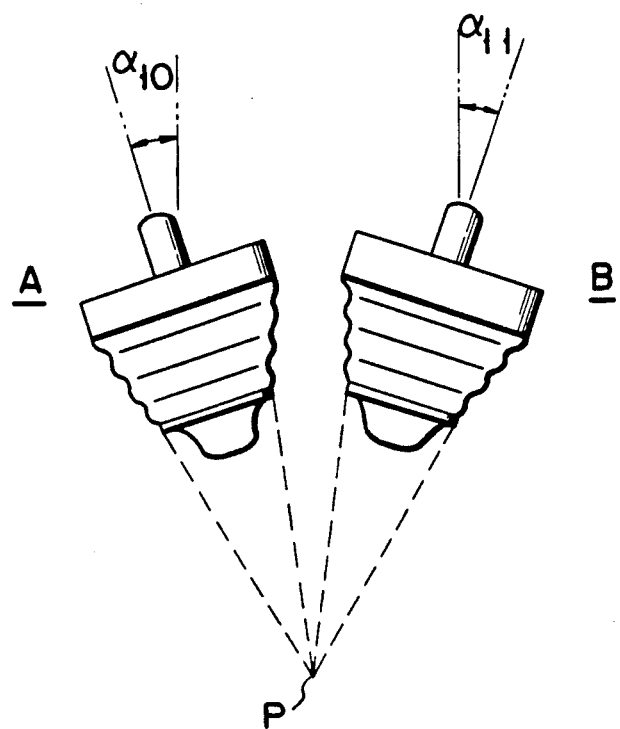
FIG. 8 shows the shock-wave oscillator section in the case where the direction of radiation of shock waves is changed.

When position A of the shock-wave oscillating section 3, where shock waves are radiated at an angle $\alpha 10$ is changed to position B where shock waves are radiated at an angle $\alpha 11$. as shown in FIG. 8, the control processor 46 outputs movement oontrol signals corresponding to the amounts of movement $\Delta X$ and $\Delta Y$ to the X-/Y-axis movement mechanism 40, outputs a movement control signal corresponding to the amount of movement $\Delta Z$ to the Z-axis movement mechanism 41, and also outputs to the second mechanism a movement control signal represented by:

$$\Delta\alpha = \alpha 11 - \alpha 10$$

Consequently, the X-/Y-axis movement mechanism 40 moves the shock-wave oscillator section 3 in the X- and Y-directions, the Z-axis movement mechanism 41 moves the shock-wave oscillator section 3 in the Z-direction, and the second rotation mechanism rotates the shock-wave oscillator section 3 in the $\alpha$-direction. The rotation in the $\beta$-direction is controlled similarly. Thus, the direction of radiation of shock waves is changed so as not to adversely affect the ribs, etc., with the focal point P of the shock-wave oscillator section 3 being set on the target. Even if the shock-wave oscillator section 3 moves, the visual field of the probe 12 always covers the target, and the probe 14 detects the target while moving. Thereafter, shock waves are radiated from the shock-wave oscillator section 3 to the target (kidney stone) and destroy it.

As has been described above, since in the sixth embodiment the X-/Y-axis movement mechanism 40 and Z-axis movement mechanism 41 move the shock-wave oscillator section 3 in the X-, Y- and Z-directions, and the first and second rotation mechanisms rotates the shockwave oscillator section 3 in the α- and β-directions. Thus, while keeping the focal point P at the target, the position of the shock-wave oscillator section 3 ca be changed and the angle of radiation of shock waves can be changed. In addition, since the amounts of movement ΔX, ΔY and ΔZ can be found from the amounts of rotational movement α and β, as is expressed in equations (26) to (28), the movement of the shock-wave oscillator section 3 can be controlled by a single two-axis type joystick.

A seventh embodiment of the present invention will now be described.

When the shock-wave oscillator section 3 is moved slightly from a given position (α1, β, Z1) by a degree represented by:

$$\sin \Delta\alpha = \Delta\alpha, \sin \Delta\beta = \Delta\beta,$$

$$\cos \Delta\alpha = 1, \cos \Delta\beta = 1,$$

the following equations can be obtained by approximation of equations (29) to (31):

$$\Delta X = Zf \cdot \Delta\beta \cdot \cos\beta_1 \cos \alpha_1 - Zf \cdot \Delta\alpha \cdot \sin\alpha_1 \sin\beta_1 \quad (29)$$

$$\Delta Y = -Zf \cdot \Delta\alpha \cdot \cos\alpha_1 \quad (30)$$

$$\Delta Z = -Zf \cdot \Delta\alpha \cdot \sin\alpha_1 \cos\beta_1 - Zf \cdot \Delta\beta \cdot \sin\beta_1 \cos\alpha_1 \quad (31)$$

These equations indicate that, if values determined by a given position are considered to be proportion constants, the values ΔX, ΔY, ΔZ, Δα, and Δβ have a linear relationship. Supposing these proportion constants are A, B, C and D, equations (29) and (31) are developed as follows:

$$\Delta X = A \cdot \Delta\beta - B \cdot \Delta\alpha \quad (32)$$

$$\Delta Y = C \cdot \Delta\alpha \quad (33)$$

$$\Delta Z = -D \cdot \Delta\beta - E \cdot \Delta\alpha \quad (34)$$

From equations (32) to (34), the amounts of movement ΔX, ΔY and ΔZ can be found by simple proportional calculations. The movement control signals corresponding to ΔX, ΔY and ΔZ are sent to the mechanism for the movements in the X-, Y-, Z-, α- and β-axes.

As described above, in the seventh embodiment, the control processor 46 has a control function using simple proportional calculations based on a trigonometric function. Thus, when the shock-wave oscillator section 3 is moved slightly, the amounts of movement ΔX, ΔY and ΔZ are calculated by a simple process, and the corresponding movement control signals can be output.

In addition, in this seventh embodiment, like in the first embodiment, the amounts of movement Δα and Δβ may be input to the control processor 46 by means of a joystick, thereby changing the direction of shock waves radiated from the shock-wave oscillator section 3.

Figure 9:
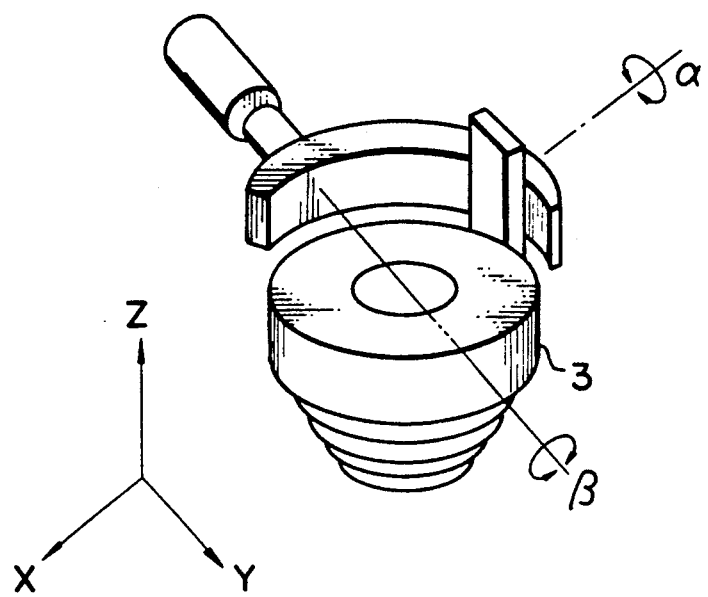
FIG. 9 shows an appearance of a curved arm, used in place of an L-shaped arm.

The present invention is not limited to the above-described embodiments, and various modifications may be made to the invention within the scope of the subject matter of the invention. For example, the L-shaped arm 37 may be replaced with a curved arm as shown in FIG. 9. Furthermore, the shock waves are not limited to ultrasonic waves.

What is claimed is:

1. A lithotripter with a shock-wave generator movement mechanism comprising:

X-/Y-/Z-axis movement means movable along X-, Y-, and Z-axes which are perpendicular to one another, said X-/Y-/Z-axis movement means including a first arm slidable along the Z-axis, and a second arm slidable along the X and Y-axes;

first rotation means, attached to said second arm of said X-/Y-/Z-axis movement means such that an end of said first rotation means is pivotable on an end portion of the second arm, said first rotation means being rotatable on the Y-axis;

second rotation means, attached to the other end of said first rotation means and rotatable on the X-axis;

a movement mechanism provided on said second rotation means and movable along a movement axis crossing an X-Y plane defined by the X- and Y axes, said movement axis being changed in accordance with the rotation of said second rotation means;

shock-wave oscillating means, provided on said movement mechanism, for generating shock waves; and control processing means for driving said X-/Y-/Z-axis movement means, said first and second rotation means, and said movement mechanism, to change the direction of radiation of the shock waves generated by said shock-wave oscillating means, while the shock-wave oscillating means is being directed to the target of treatment.

2. A lithotripter with a shock-wave generator movement mechanism comprising:

X-/Y-/Z-axis movement means movable along X-, Y-, and Z-axes which are perpendicular to one another, said X-/Y-/Z-axis movement means including X-/Y-movement mechanism, a Z-direction column mounted on the X-/Y-movement mechanism, and a moving body slidable on the Z-directional column.

first rotation means, attached to said moving body of said X-/Y-/Z-axis movement means such that an end of said first rotation means is pivotable on an end portion of the moving body, said first rotation means being rotatable on the Y-axis;

second rotation means, attached to the other end of said first rotation means and rotatable on the X-axis;

shock-wave oscillating means, provided on said movement mechanism, for generating shock waves; and control processing means for driving said X-/Y-/Z-axis movement means, and said first and second rotation means, to change the direction of radiation of the shock waves generated by said shock-wave oscillating means, while the shock-wave oscillating means is being directed to the target of treatment; said control processing means including:

calculating means for calculating the amounts of movement of said X-/Y-/Z-axis movement means, said first and second rotation means, and said movement mechanism, from the XY position and angle of the shock-wave oscillating means and the position of the movement mechanism, before the movement of the shock-wave oscillating means, and from the XY position and angle of the shock-wave oscillating means and the position of the movement mechanism, after the movement of the shock-wave oscillating means;

movement means control means for generating a rotation control signal to rotate said first and second rotating means in accordance with the calculated amounts of movement of said first and second rotation means and for generating a movement mechanism control signal to move said movement mechanism along the movement axis crossing the X-Y plane in accordance with the calculated amount of movement of said movement.

3. A lithotripter with a shock-wave generator movement mechanism comprising:

X-/Y-/Z-axis movement means movable along X-, Y-, and Z-axes which are perpendicular to one another, said X-/Y-/Z-axis movement means including a first arm slidable along the Z-axis, and a second arm slidable along the X and Y-axes;

first rotation means, attached to said second arm of said X-/Y-/Z-axis movement means such that an end of said first rotation means is pivotable on an end portion of the second arm, said first rotation means being rotatable on the Y-axis;

second rotation means, attached to the other end of said first rotation means and rotatable on the X-axis; a movement mechanism provided on said second rotation means and movable along a movement axis crossing an X-Y plane defined by the X- and Y axes, said movement axis being changed in accordance with the rotation of said second rotation means;

shock-wave oscillating means, provided on said movement mechanism, for generating shock waves; and control processing means for driving said X-/Y-/Z-axis movement means, said first and second rotation means, and said movement mechanism, to change the direction of radiation of the shock waves generated by said shock-wave oscillating means, while the shock-wave oscillating means is being directed to the target of treatment, said control processing means including:

calculating means for calculating the amount of movement of said X-/Y-/Z-axis movement means, said first and second rotation means, and said movement mechanism, from the XY position and angle of the shock-wave oscillating means and the position of the movement mechanism, before the movement of the shock-wave oscillating means, and from the XY position and angle of the shock-wave oscillating means and the position of the movement mechanism, after the movement of the shock-wave oscillating means;

movement means control means for generating a movement means control signal to move said second arm in the X- and Y-directions in accordance with the calculated amount of movement of said X-/Y-/Z-axis movement means;

rotation control means for generating a rotation control signal to rotate said first and second rotating means in accordance with the calculated amounts of movement of said first and second rotation means; and movement mechanism control means for generating a movement mechanism control signal to move said movement mechanism along the omvement axis crossing the X-Y plane in accordance with the calculated amount of movement of said movement.

4. A lithotripter with a shock-wave generator movement mechanism comprising;

X-/Y-/Z-axis movement means movable along X-, Y-, and Z-axes which are perpendicular to one another, said X-/Y-/Z-axis movement means including a first arm slidable along the Z-axis, and a second arm slidable along the X and Y-axes;

first rotation means, attached to said second arm of said X-/Y-/Z-axis movement means such that an end of said first rotation means is pivotable on an end portion of the second arm, said first rotation means being rotatable on the Y-axis;

second rotation means, attached to the other end of said first rotation means and rotatable on the X-axis; a movement mechanism provided on said second rotation means and movable along a movement axis crossing an X-Y plane defined by the X- and Y axes, said movement axis being changed in accordance with the rotation of said second rotation means;

shock-wave oscillating means, provided on said movement mechanism, for generating shock waves; and control processing means for driving said X-/Y-/Z-axis movement means, said first and second rotation means, and said movement mechanism, to change the direction of radiation of the shock waves generated by said shock-wave oscillating means, while the shock-wave oscillating means is being directed to the target of treatment, said control processing means including:

calculating means for calculating the amounts of movement of said X-/Y-/Z-axis movement means, said first and second rotation means, and said movement mechanism, from the XY position and angle of the shock-wave oscillating means and the position of the movement mechanism, before the movement of the shock-wave oscillating means, and from the XY position and angle of the shock-wave oscillating means and the position of the movement mechanism, after the movement of the shock-wave oscillating means;

movement means control means for generating a movement means control signal to move said second arm in the X- and Y-directions in accordance with the calculated amount of movement of said X-/Y-/Z-axis movement means;

rotation control means for generating a rotation cotnrol siganl to rotate said first and second rotating means in accordance with the calculated amounts of movement of said first and second rotation means, while said movement means control means is performing the control operation; and movement mechanism control means for generating a movement mechanism control signal to move said movement mechanism along the movement axis crossing the X-Y plane in accordance with the calculated amount of movement of said movement, after the control operations of said movement means control means and said rotation control means have been completed.

5. A lithotripter with a shock-wave generator movement mechanism comprising:

X-/Y-/Z-axis movement means movable along X-, Y-, and Z-axes which are perpendicular to one another, said X-/Y-/Z-axis movement means including a first arm slidable along the Z-axis, and a second arm slidable along the X and Y-axes;

first rotation means, attached to said second arm of said X-/Y-/Z-axis movement means such that an end of said first rotation means is pivotable on an end portion of the second arm, said first rotation means being rotatable on the Y-axis;

second rotation means, attached to the other end of said first rotation means and rotatable on the X-axis; a movement mechanism provided on said second rotation means and movable along a movement axis crossing an X-Y plane defined by the X- and Y axes, said movement axis being changed in accordance with the rotation of said second rotation means;

shock-wave oscillating means, provided on said movement mechanism, for generating shock waves; and control processing means for driving said X-/Y-/Z-axis movement means, said first and second rotation means, and said movement mechanism, to change the direction of radiation of the shock waves generated by said shock-wave oscillating means, while the shock-wave oscillating means is being directed to the target of treatment, said control processing means including:

calculating means for calculating the amounts of movement of said X-/Y-/Z-axis movement means, said first and second rotation means, and said movement mechanism, from the XY position and angle of the shock-wave oscillating means and the position of the movement mechanism, before the movement of the shock-wave oscillating means, and from the XY position and angle of the shock-wave oscillating means and the position of the movement mechanism, after the movement of the shock-wave oscillating means, by multiplying a constant with the difference between the angle before the movement and the angle after the movement by trigonometric function approximation;

movement means control means for generating a movement means control signal to move said second arm in the X- and Y-directions in accordance with the calculated amount of movement of said X-/Y-/Z-axis movement means;

rotation control means for generating a rotation control signal to rotate said first and second rotating means in accordance with the calculated amounts of movement of said first and second rotation means; and movement mechanism control means for generating a movement mechanism control signal to move said movement accordance with the calculated amount of movement of said movement.

6. A lithotripter with a shock-wave generator movement mechanism comprising:

X-/Y-/Z-axis movement means movable along X-, Y-, and Z-axes which are perpendicular to one another, said X-/Y-/Z-axis movement means including a first arm slidable along the Z-axis, and a second arm slidable along the X and Y axes;

first rotation means, attached to said second arm of said X-/Y-/Z-axis movement means such that an end of said first rotation means is pivotable on an end portion of the second arm, said first rotation means being rotatable on the Y-axis;

second rotation means, attached to the other end of said first rotation means and rotatable on the X-axis;

a movement mechanism provided on said second rotation means and movable along a movement axis crossing an X-Y plane defined by the X- and Y axes, said movement axis being changed in accordance with the rotation of said second rotation means;

shock-wave oscillating means, provided on said movement mechanis, for generating shock waves; and control processing means for driving said X-/Y-/Z-axis movement means, said first and second rotation means, and said movement mechanism, to change the direction of radiation of the shock waves generated by said shock-wave oscillating means, while the shock-wave oscillating means is being directed to the target of treatment, said control processing means including:

calculating means for calculating the amounts of movement of said X-/Y-/Z-axis movement means, said first and second rotation means, and said movement mechanism, from the XY position and angle of the shock-wave oscillating means and the position of the movement mechanism, before the movement of the shock-wave oscillating means, and from the XY position and angle of the shock-wave oscillating means and the position of the movement mechanism, after the movement of the shock-wave oscillating means, by multiplying a constant with the difference between the angle before the movement and the angle after the movement by trigonometric function approximation, and adding another constant to the multiplied value; movement means control means for generating a movement means control signal to move said second arm in the X- and Y-directions in accordance with the calculated amount of movement of said X-/Y-/Z-axis movement means;

rotation control means for generating a rotation control signal to rotate said first and second rotating means in accordance with the calculated amounts of movement of said first and second rotation means; and movement mechanism control means for generating a movement mechanism control signal to move said movement mechanism along the movement axis crossing the X-Y plane in accordance with the calculated amount of movement of said movement.

7. A lithotripter with a shock-wave generator movement mechanism comprising:

X-/Y-/Z-axis movement means movable along X-, Y-, and Z-axes which are perpendicular to one another, said X-/Y-/Z-axis movement means including X-/Y-movement mechanism, a Z-directional column mounted on the X-/Y-movement mechanism, and a moving body slidable on the Z-directional column;

first rotation means, attached to said movign body of said X-/Y-/Z-axis movement means such that an end of said first rotation means is pivotable on an end portion of the moving body, said first rotation means being rotatable on the Y-axis;

second rotation means, attached to the other end of said first rotation means and rotatable on the X-axis;

shock-wave oscillating means, provided on said movement mechanism, for generating shock waves; and control processing means for driving said X-/Y-/Z-axis movement means, and said first and second rotation means, to change the direction of radiation of the shock waves generated by said shock-wave oscillating means, while the shock-wave oscillating means is being directed to the target of treatment, said control processing means including:

calculating means for calculating the amounts of movement of said X-/Y-/Z-axis movement means, said first and second rotation means, and said movement mechanism, from the XY position and angle of the shock-wave oscillating means and the shock-wave oscillating means, and from the XY position and angle of the shock-wave oscillating means and the position of the movement mechanism, after the movement of the shock-wave oscillating means;

rotation control means for generating a rotation cotnrol signal to rotate said first and second rotating means in accordance with the calculated amounts of movement of said first and second rotation means; and movement mechanism control means for generating a movement mechanism control signal to move said movement mechanism along the movement axis crossing the X-Y plane in accordance with the calculated amount of movement of said movement.

8. A lithotripter with a shock-wave generator movement mechanism comprising:

X-/Y-/Z-axis movement means movable along X-, Y-, and Z-axes which are perpendicular to one another, said X-/Y-/Z-axis movement means including X-/Y-movement mechanism, a Z-directional column mounted on the X-/Y-movement mechanism, and a moving body slidable on the Z-directional column;

first rotation means, attached to said moving body of said X-/Y-/Z-axis movement means such that an end of said first rotation means is pivotable on an end portion of the moving body, said first rotation means being rotatable on the Y-axis;

second rotation means, attached to the other end of said first rotation means and rotatable on the X-axis;

shock-wave oscillating means, provided on said movement mechanism, for generating shock waves; and control processing means for driving said X-/Y-/Z-axis movement means, and said first and second rotation means, to change the direction of radiation of the shock waves generated by said shock-wave oscillating means, while the shock-wave oscillating means is being directed to the target of treatment, said control processing means including:

calculating means for calculating the amounts of movement of said X-/Y-/Z-axis movement means, said first and second rotation means, and said movement mechanism, from the XY position and angle of the shock-wave oscillating means and the position of the movement mechanism, before the movement of the shock-wave oscillating means, and from the XY position and angle of the shock-wave oscillating means and the position of the movement mechanism, after the omvement of the shock-wave oscillating means, by multiplying a constant with the difference between the angle before the movement and the angle after the movement by trigonometric function approximation;

rotation control means for generating a rotation control signal to rotate said first and second rotating means in accordance with the calculated amounts of movement of said first and second rotation means; and movement mechanism control means for generating a movement mechanism control signal to move said movement mechanism along the movement axis crossing the X-Y plane in accordance with the calculated amount of movement of said movement.

* * * * *